United States Patent [19]

Ichiroku et al.

[11] Patent Number: 5,473,091

[45] Date of Patent: Dec. 5, 1995

[54] QUATERNARY PHOSPHORUS COMPOUNDS AND THEIR PREPARATION

[75] Inventors: Nobuhiro Ichiroku; Koji Futatsumori; Kazuhiro Arai; Miyuki Wakao; Toshio Shiobara, all of Gunma, Japan

[73] Assignee: Shin-Etsu Chemical Co., Ltd., Tokyo, Japan

[21] Appl. No.: 399,473

[22] Filed: Mar. 7, 1995

[30]   Foreign Application Priority Data

Mar. 7, 1994 [JP] Japan .................................. 6-062030

[51] Int. Cl.⁶ ..................................................... C07F 5/02
[52] U.S. Cl. ........................................................... 558/72
[58] Field of Search ................................................ 558/72

[56] References Cited

U.S. PATENT DOCUMENTS 5,254,706  10/1993  Spielvogel et al. ........................ 558/72

OTHER PUBLICATIONS

JP-B 45491/1981, Epoxy! resin . . . tetraphenylborate.

CA 96:199878c Aryloxyphosphonium salts. p. 692, 1982.

*Primary Examiner*—Joseph K. McKane
*Attorney, Agent, or Firm*—Birch, Stewart, Kolasch & Birch

[57]   ABSTRACT

A novel quaternary phosphorus compound is a salt between tetraphenyl borate and a phosphonium having an aromatic group attached to a phosphorus atom through an oxygen atom. It is blended with an epoxy resin as a curing catalyst to form an epoxy resin composition which flows smoothly and quickly cures into a product having improved moisture resistance and adhesion.

1 Claim, 1 Drawing Sheet

QUATERNARY PHOSPHORUS COMPOUNDS AND THEIR PREPARATION

BACKGROUND OF THE INVENTION

1. Field of the Invention

This invention relates to a quaternary phosphorus compound having a salt structure between tetraphenyl borate and a phosphonium having an aromatic group attached to a phosphorus atom through an oxygen atom and useful as a curing catalyst for epoxy resin compositions. It also relates to a method for preparing the compound and a curing catalyst.

2. Prior Art

From the past, curing catalysts are blended in epoxy resin compositions comprising an epoxy resin and a phenolic resin as a curing agent. Conventional curing catalysts are imidazole derivatives, tertiary amine compounds, tertiary phosphine compounds and derivatives thereof. These curing agents, however, are less shelf stable and induce a viscosity rise when kneaded with epoxy resins, thus adversely affecting the flow of the molding composition.

JP-B 45491/1981 discloses a compound obtained by heat treating a novolak type phenolic resin and tetraphenylphosphonium tetraphenylborate (to be abbreviated as TPP-K, hereinafter) at a temperature above the softening point of the novolak type phenolic resin and continuing the heat treatment until the resin system becomes yellowish brown or brown color. By using this compound as a curing agent for an epoxy resin, there is obtained an epoxy resin composition which is shelf stable and cures into a product having improved moisture resistance. However, since this curing catalyst is less active and slow curing, it must be used in large amounts, rather detracting from the shelf stability of epoxy resin compositions.

TPP-K itself is also a useful curing catalyst which is fully potential in that reaction takes place from a certain temperature, but slow curing. Triphenylphosphine which is often used in the art is quick curing, but less shelf stable.

Conventional curing catalysts are difficult to provide an epoxy resin composition which is shelf stable, smoothly flowing, quick curing, and moisture resistant.

SUMMARY OF THE INVENTION

Therefore, an object of the present invention is to provide a quaternary phosphorus compound which is advantageously blended with an epoxy resin to form a smoothly flowing, quick curing epoxy resin composition which cures into a product having improved moisture resistance and adhesion. Another object is to provide a method for preparing the same. A further object is to provide a curing catalyst.

We have found that when a quaternary phosphorus compound of the following general formula (5) is mixed with an aromatic compound having a phenolic hydroxyl group of the following general formula (6) or (7) at an elevated temperature, substitution reaction takes place between the aromatic ring attached to a phosphorus atom in the quaternary phosphorus compound of formula (5) and the aromatic compound having a phenolic hydroxyl group, forming a quaternary phosphorus compound of the structure having an aromatic ring attached to a phosphorus atom through an oxygen atom represented by the following general formula (1). This quaternary phosphorus compound is effective as a curing catalyst for an epoxy resin combined with a phenolic resin as a curing agent. It is fully potential in that reaction takes place from a certain temperature as compared with the conventional triphenylphosphine catalyst. It is more active and more reactive than the TPP-K catalyst. It is well compatible with resins. An epoxy resin composition having the quaternary phosphorus compound of formula (1) blended as a curing catalyst is shelf stable, smoothly flowing and quick curing and cures into a product having improved moisture resistance and adhesion.

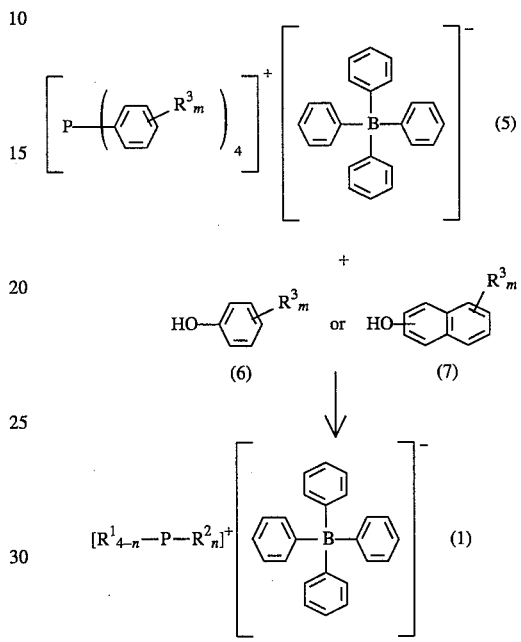

In the formulae, $R^1$ is a group of the formula (2) shown above, $R^2$ is a group of the formula (3) or (4) shown above, n is an integer of 1 to 4, $R^3$ is a monovalent hydrocarbon group having 1 to 6 carbon atoms, and m is an integer of 0 to 3. It is to be noted tat in formulae (7) and (4), when m is at least 1, $R^3$ may be attached to either one or both of the aromatic ring having —OH or —O— and the aromatic ring free of —OH or —O—.

Accordingly, the present invention in a first aspect provides a quaternary phosphorus compound of formula (1). In a second aspect, the invention provides a method for preparing a quaternary phosphorus compound of formula (1) by mixing for reaction a quaternary phosphorus compound of formula (5) with at least one compound selected from compounds of formulae (6) and (7) at a temperature of 120° to 250° C. In a third aspect, the invention provides a curing catalyst in the form of a quaternary phosphorus compound of formula (1).

DETAILED DESCRIPTION OF THE INVENTION

Figure 1:
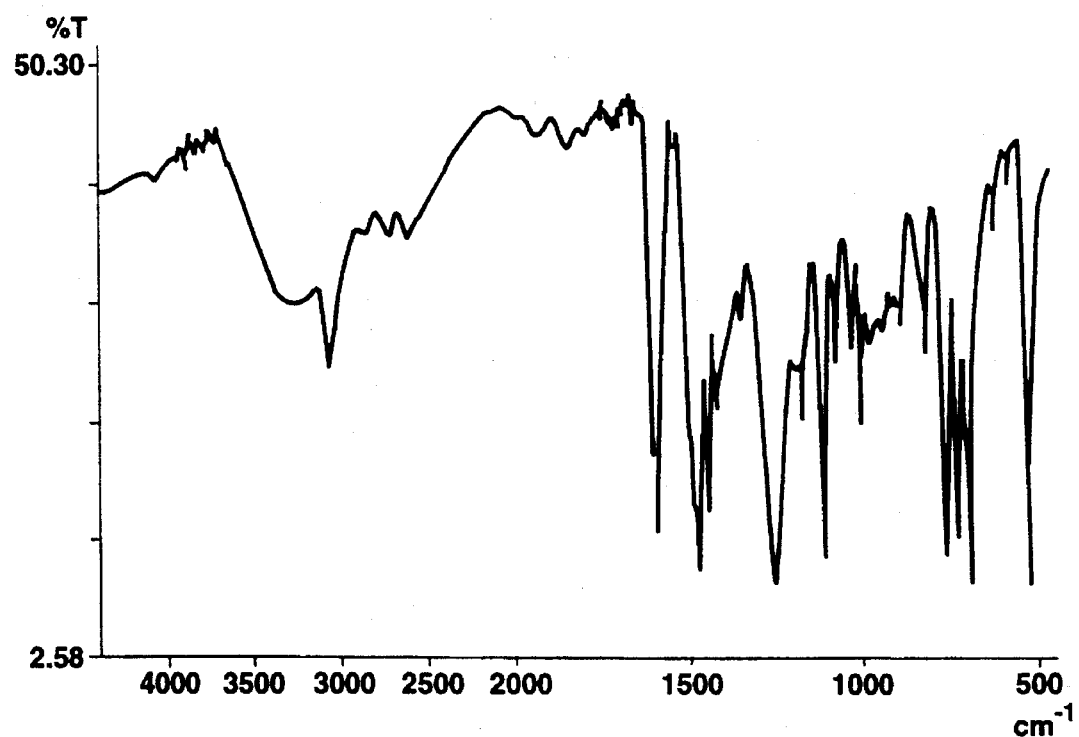
FIG. 1 diagrammatically illustrates an IR absorption spectrum of a quaternary phosphorus compound obtained in Example 1.

The present invention provides a quaternary phosphorus compound of the following general formula (1).

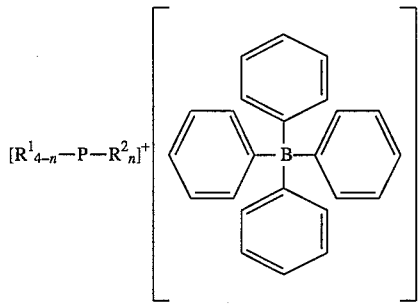

In formula (1), $R^1$ is a group of the following formula (2).

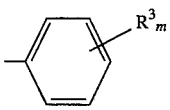

$R^2$ is a group of the following formula (3) or (4).

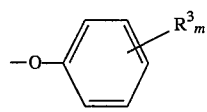

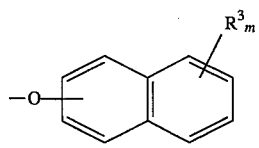

Letter n is an integer of 1 to 4.

In formulae (2), (3) and (4), $R^3$ is a monovalent hydrocarbon group having 1 to 6 carbon atoms, and m is an integer of 0 to 3. It is to be noted that in formula (4), when m is at least 1, $R^3$ may be attached to either one or both of the aromatic ring having —O— and the aromatic ring free of —O—.

Illustrative, non-limiting, examples of the quaternary phosphorus compound are given below.

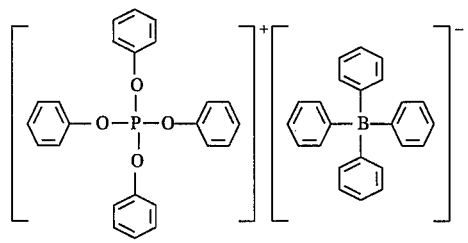

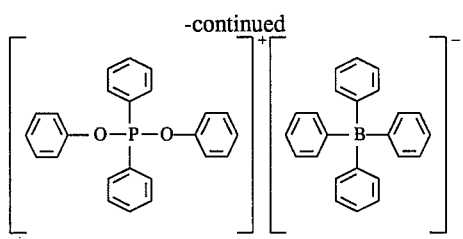

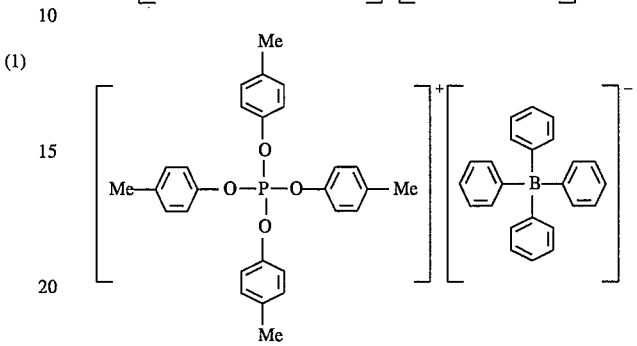

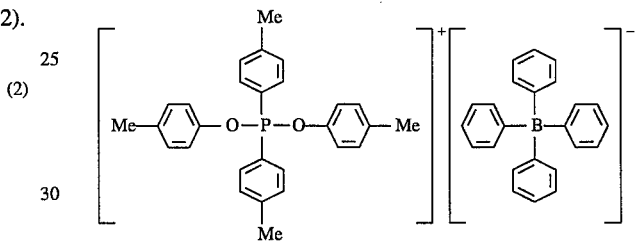

Note that Me is methyl.

The quaternary phosphorus compound of formula (1) is prepared by mixing for reaction a quaternary phosphorus compound of formula (5) with at least one compound selected from compounds of formulae (6) and (7) at a temperature of 120° to 250° C., preferably 160° to 200° C. Then at least one of the four aromatic rings attached to the phosphorus atom in the quaternary phosphorus compound of formula (5) is replaced by at least one aromatic ring having an oxygen atom, forming a quaternary phosphorus compound of formula (1).

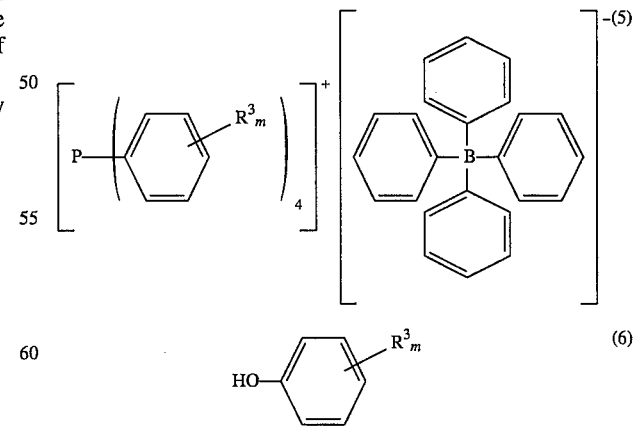

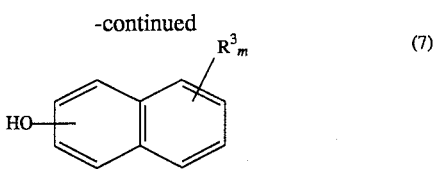
(7)

In formulae (5), (6) and (7), $R^3$ is a monovalent hydrocarbon group having 1 to 6 carbon atoms, and m is an integer of 0 to 3. It is to be noted that in formula (7), when m is at least 1, $R^3$ may be attached to either one or both of the aromatic ring having —OH and the aromatic ring free of —OH.

Substitution reaction is very slow at reaction temperatures of lower than 120° C. Reaction temperatures of higher than 250° C. induce decomposition reaction of the quaternary phosphorus compound of formula (5), failing to produce an end reaction product in high yields.

If oxygen is present in the reaction system, the quaternary phosphorus compound is oxidized with oxygen to convert from P(III) to P(V), allowing for decomposition reaction of the quaternary phosphorus compound to take place. It is desirable to fully remove oxygen from the reaction system, namely to carry out reaction in an inert atmosphere such as nitrogen.

Since this substitution reaction is believed to be of the SnZ type wherein a solvent can have influence on the substitution reaction, a suitable solvent should preferably be selected pursuant to an end product. The solvents used herein include protic solvents, aprotic solvents, and aromatic compounds having a phenolic hydroxyl group represented by formulae (6) and (7) themselves.

The use of protic solvents increases the activation energy of substitution reaction to slow down the reaction because an aromatic carbanion which is a nucleophile is more effectively stabilized than a transition state of an intermediate. Also the use of protic solvents is advantageous in producing a tetra-substituted compound because, due to the high activation energy, the nucleophile attacks a more positively charged phosphorus atom and thus more preferentially attacks a di-substituted compound than a mono-substituted compound, a tri-substituted compound than the di-substituted compound, resulting in preferential formation of a tetra-substituted compound. It is then recommended to use at least 4 mol, preferably 5 to 20 mol of the aromatic compound having a phenolic hydroxyl group per mol of the quaternary phosphorus compound of formula (5). Examples of the protic solvent include alcohols such as cyclohexanol, methanol and ethanol and carboxylic acids such as acetic acid.

Since aprotic solvents, on the other hand, do not contribute to the stabilization of either an aromatic carbanion nucleophile or a transition state of reaction, the activation energy is lower than when protic solvents are used, resulting in an increased reaction rate. Also the use of aprotic solvents is advantageous for producing mono- to tri-substituted compounds because selectivity to the substrate is reduced due to the low activation energy, and nucleophilic attack occurs in a substantially equal proportion. It is then recommended to use 1 to 4 mol of the aromatic compound having a phenolic hydroxyl group per mol of the quaternary phosphorus compound of formula (5) in accordance with the degree of substitution of an end substituted compound. Examples of the aprotic solvent include various hydrocarbons, carbon tetrachloride, dioxane, ether, dimethylsulfoxide, and dimethylsulfonate.

When aromatic compounds having a phenolic hydroxyl group represented by formulae (6) and (7) themselves are used as the solvent, the reaction system is a protic solvent system. Since an aromatic carbanion which is a nucleophile is present in full excess and these aromatic compounds are correlated to the solvation of a quaternary phosphorus compound of formula (5) as a reaction substrate and are fully excessive from the standpoint of a local concentration, a tetra-substituted compound is selectively produced at a fully high reaction rate. Therefore this reaction system is suited for forming a tetra-substituted compound.

The substitution reaction is generally carried out for about ½ to 4 hours. After the solvent is removed, the reaction product is extracted with chloroform, toluene or any suitable solvent and dried, obtaining an end quaternary phosphorus compound of formula (1). If the reaction product is a mixture of products having different degree of substitution, the individual products may be isolated, for example, by column separation.

The quaternary phosphorus compound of formula (1) is useful as a curing catalyst for a curable resin composition comprising an epoxy resin and a phenolic resin. When it is blended in a curable resin composition, typically an epoxy resin composition, the resulting composition is storage stable, smoothly flowing and quick curing and cures into a product having improved moisture resistance.

The quaternary phosphorus compound of the invention is a tetraphenylphosphine wherein 1 to 4 of the four aromatic rings attached to the phosphorus atom are replaced by 1 to 4 aromatic rings attached to the phosphorus atom through an oxygen atom. By selecting the degree of substitution, the activity and potentiality of the compound as a curing catalyst can be controlled. More illustratively, a higher degree of substitution leads to a curing catalyst having higher activity and potentiality whereas a lower degree of substitution leads to a curing catalyst having relatively lower activity and potentiality.

Where the quaternary phosphorus compound of formula (1) is used as a curing catalyst for a curable resin composition comprising an epoxy resin and a phenolic resin, it is generally blended in an amount of about 5 to 30 parts, preferably about 10 to 20 parts by weight per 100 parts by weight of the epoxy and phenolic resins combined.

There has been described a quaternary phosphorus compound which is useful as a curing catalyst. It is advantageously blended in a curable resin composition comprising an epoxy resin and a phenolic resin. The resulting composition is storage stable, smoothly flows and quickly cures into a product having improved moisture resistance and adhesion. The inventive method ensures easy preparation of such a quaternary phosphorus compound.

EXAMPLE

Examples of the present invention are given below by way of illustration and not by way of limitation.

Example 1

A reactor was charged with 16.3 g (0.025 mol) of TPP-K, 40.0 g (0.425 mol) of phenol and 250 ml of cyclohexanol as a protic solvent and heated to an internal temperature of 161° C. or the boiling point of cyclohexanol (external temperature 170° C.). Reaction was effected for 3 hours in a nitrogen atmosphere. The unreacted phenol and cyclohexanol reaction solvent were removed from the reaction solution in vacuum (2 mmHg) at 100° C. Extraction with chloroform yielded 1.47 g (yield 5%) of a quaternary phosphorus compound of the following formula (1a) as a clear brown solid having a melting point of 82° C. As the unreacted compound, 14.8 g of the TPP-K reactant was recovered (unreacted rate 90%).

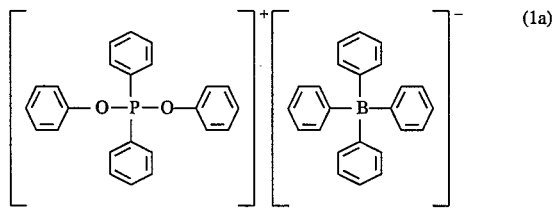

(1a)

The quaternary phosphorus compound thus obtained was examined by elemental analysis, NMR, and IR absorption spectrometry. The results of elemental analysis are shown below. FIG. 1 shows the IR absorption spectrum in which an absorption band characteristic of a P—O bond was observed in proximity to 1100 to 1200 $cm^{-1}$. With these data, the compound was identified to have formula (1a) as shown above.

| | Elemental analysis | | | |
|---|---|---|---|---|
| | C | H | P | B |
| Calcd. (%) | 79.9 | 5.58 | 4.29 | 1.50 |
| Found (%) | 82.1 | 5.21 | 4.40 | 1.32 |

Example 2

A reactor was charged with 16.3 g (0.025 mol) of TPP-K and 40.0 g (0.425 mol) of phenol as a reaction substrate and protic solvent and heated to an internal temperature of 182° C. or the boiling point of phenol (external temperature 200° C.). Reaction was effected for 3 hours in a nitrogen atmosphere. The unreacted phenol was removed from the reaction solution in vacuum (2 mmHg) at 100° C. Extraction with chloroform yielded 34.3 g (yield 95%) of a quaternary phosphorus compound of the above-described formula (1a) as a clear brown solid having a melting point of 82° C. As the unreacted compound, 0.6 g of the TPP-K reactant was recovered (unreacted rate 2.5%).

The quaternary phosphorus compound thus obtained was examined by elemental analysis, NMR, and IR absorption spectrometry. The results of elemental analysis are shown below. In the IR absorption spectrum, an absorption band characteristic of a P—O bond was observed in proximity to 1100 to 1200 $cm^{-1}$. With these data, the compound was identified to have formula (1a) as shown above.

| | Elemental analysis | | | |
|---|---|---|---|---|
| | C | H | P | B |
| Calcd. (%) | 79.9 | 5.58 | 4.29 | 1.50 |
| Found (%) | 78.1 | 5.51 | 4.10 | 1.62 |

Example 3

A reactor was charged with 16.3 g (0.025 mol) of TPP-K, 9.3 g (0.05 mol) of phenol and 250 ml of dimethylsulfonate as an aprotic solvent and heated to an internal temperature of 182° C. or the boiling point of dimethylsulfonate (external temperature 190° C.). Reaction was effected for 5 hours in a nitrogen atmosphere. The unreacted phenol and dimethylsulfonate reaction solvent were removed from the reaction solution in vacuum (2 mmHg) at 100° C. Extraction with chloroform yielded 16.4 g (yield 92%) of a quaternary phosphorus compound of the following formula (1b) as white columnar crystals having a melting point of 152° C.

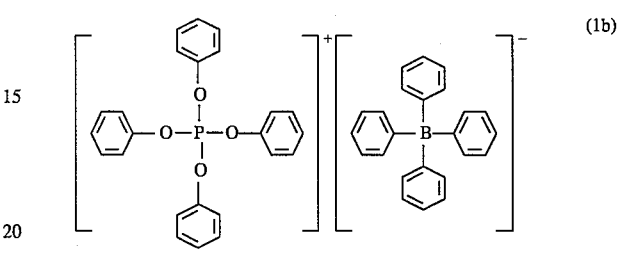

(1b)

The quaternary phosphorus compound thus obtained was examined by elemental analysis, NMR, and IR absorption spectrometry. The results of elemental analysis are shown below. In the IR absorption spectrum, an absorption band characteristic of a P—O bond was observed in proximity to 1100 to 1200 $cm^{-1}$. With these data, the compound was identified to have formula (1b) as shown above.

| | Elemental analysis | | | |
|---|---|---|---|---|
| | C | H | P | B |
| Calcd. (%) | 83.5 | 5.84 | 4.48 | 1.57 |
| Found (%) | 81.0 | 5.92 | 4.62 | 1.89 |

Example 4

Reaction was effected as in Example 2 except that 45.9 g (0. 425 mol) of p-cresol was used instead of phenol and the reactor was heated to an internal temperature of 202° C. or the boiling point of p-cresol. There was obtained 18.3 g (yield 95%) of a quaternary phosphorus compound of the following formula (1c) as a clear brown solid having a melting point of 86° C.

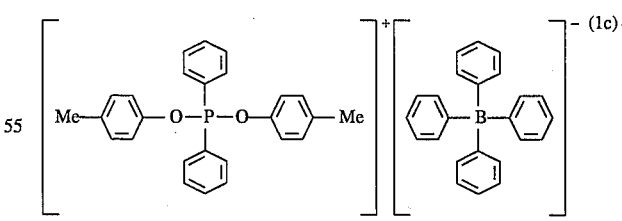

(1c)

Figure 2:
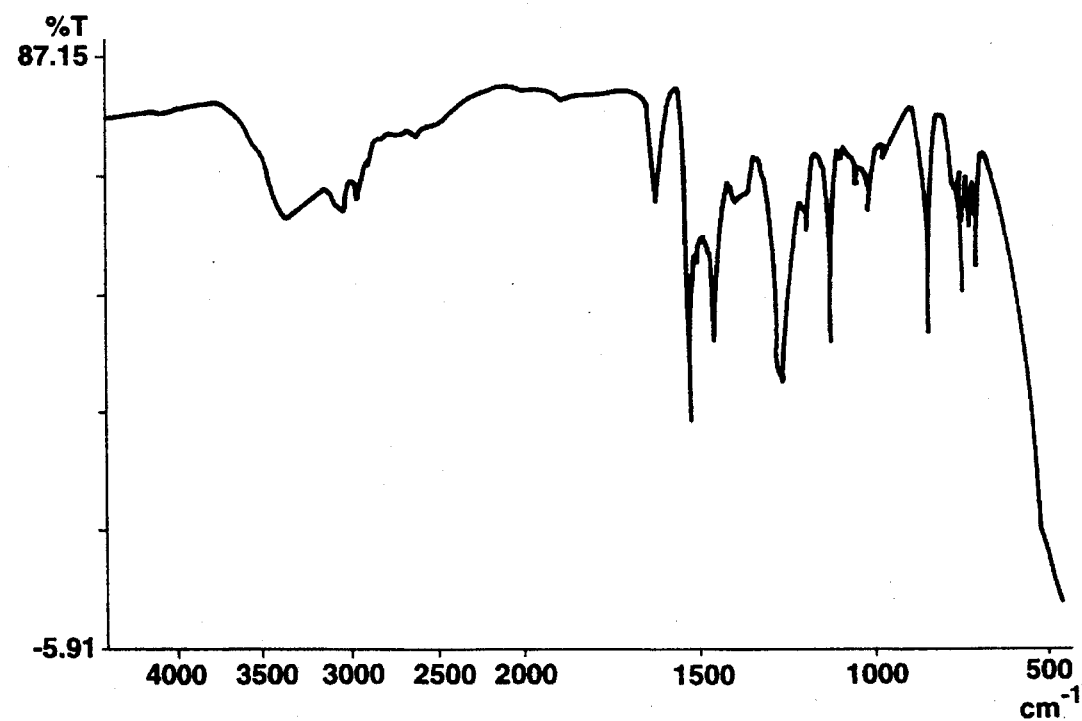
FIG. 2 diagrammatically illustrates an IR absorption spectrum of a quaternary phosphorus compound obtained in Example 4.

The quaternary phosphorus compound thus obtained was examined by elemental analysis, NMR, and IR absorption spectrometry. The results of elemental analysis are shown below. FIG. 2 shows the IR absorption spectrum in which an absorption band characteristic of a P—O bond was observed in proximity to 1100 to 1200 $cm^{-1}$. With these data, the compound was identified to have formula (1C) as shown above.

|            | Elemental analysis |      |      |      |
|------------|------|------|------|------|
|            | C    | H    | P    | B    |
| Calcd. (%) | 80.2 | 6.21 | 3.98 | 1.39 |
| Found (%)  | 78.0 | 6.60 | 4.10 | 1.21 |

Example 5

Reaction was effected as in Example 3 except that 5.4 g (0.05 mol) of p-cresol was used instead of phenol and the reactor was heated to an internal temperature of 182° C. or the boiling point of dimethylsulfonate. There was obtained 17.0 g (yield 96%) of a quaternary phosphorus compound of the following formula (1d) as white columnar crystals having a melting point of 148° C.

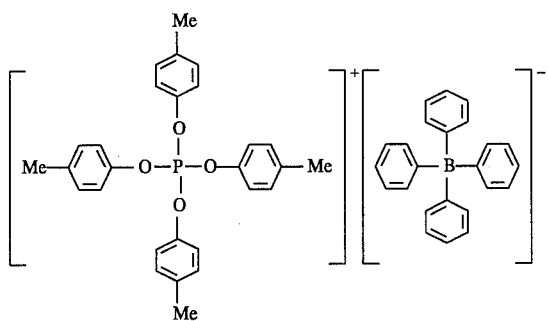
(1d)

The quaternary phosphorus compound thus obtained was examined by elemental analysis, NMR, and IR absorption spectrometry. The results of elemental analysis are shown below. In the IR absorption spectrum, an absorption band characteristic of a P—O bond was observed in proximity to 1100 to 1200 cm$^{-1}$. With these data, the compound was identified to have formula (1d) as shown above.

|            | Elemental analysis |      |      |      |
|------------|------|------|------|------|
|            | C    | H    | P    | B    |
| Calcd. (%) | 83.6 | 6.17 | 4.31 | 1.50 |
| Found (%)  | 84.7 | 6.60 | 4.15 | 1.52 |

Example 6 & Comparative Example

Using the above-prepared quaternary phosphorus compounds as a curing catalyst, epoxy resin compositions were prepared. They were measured for gelling time and analyzed by differential scanning calorimetry (DSC). For comparison purposes, epoxy resin compositions were prepared using triphenylphosphine and TPP-K as a curing catalyst.

The epoxy resin compositions contained an epoxy resin and a phenolic resin as shown below in amounts as shown in Table 1. The curing catalyst was used in an amount of 0.5 mmol per 100 grams of the epoxy and phenolic resins combined. The mixture was melt mixed at 100° C. for 2 minutes and comminuted so as to pass a #80 screen.

Epoxy resin

It was an epoxidized bisphenol derivative of the following structural formula having a softening point of 105° C. and an epoxy equivalent of 190 (YX4000H by Yuka Shell Epoxy K.K.).

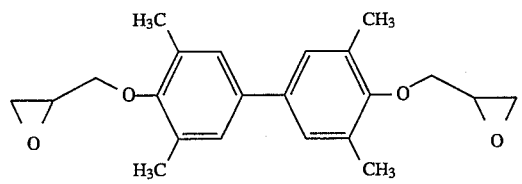

Phenolic resin

It was a naphthalene skeleton phenolic resin of the following structural formula having a softening point of 108°–112° C. and a hydroxyl equivalent of 140 (Kayahard NHN by Nihon Kayaku K.K.).

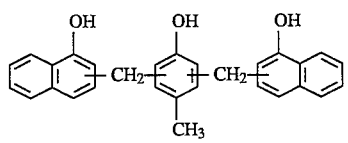

The gelling time was a curing start time (sec.) when an epoxy resin composition was heated at 175° C. A shorter gelling time indicates quicker curing.

DSC indicates the exothermic peak temperature when an epoxy resin composition was heated from 30° C. to 250° C. at a rate of 10.0° C./min. A higher temperature indicates better potentiality.

The results are shown in Table 1. The amounts of the respective components are expressed in gram.

TABLE 1

|  | Example | | | | Comparative Example | |
|---|---|---|---|---|---|---|
|  | No. 1 | No. 2 | No. 3 | No. 4 | No. 5 | No. 6 |
| Epoxy resin | 58.4 | 58.4 | 58.4 | 58.4 | 58.4 | 58.4 |
| Phenolic resin | 41.6 | 41.6 | 41.6 | 41.6 | 41.6 | 41.6 |
| Curing catalyst |  |  |  |  |  |  |
| Compound of Example 2 | 0.44 | 0 | 0 | 0 | 0 | 0 |
| Compound of Example 3 | 0 | 0.42 | 0 | 0 | 0 | 0 |
| Compound of Example 4 | 0 | 0 | 0.48 | 0 | 0 | 0 |
| Compound of Example 5 | 0 | 0 | 0 | 0.44 | 0 | 0 |
| Triphenylphosphine | 0 | 0 | 0 | 0 | 0.16 | 0 |
| TPP - K | 0 | 0 | 0 | 0 | 0 | 0.40 |
| Gelling time (sec.) | 18 | 25 | 19 | 27 | 18 | 57 |
| DSC peak temp. (°C.) | 141 | 172 | 142 | 175 | 134 | 181 |

As seen from Table 1, the epoxy resin compositions using the quaternary phosphorus compounds within the scope of the invention (Nos. 1 to 4) are improved in potentiality over the composition using triphenylphosphine (No. 5) and in quick curing over the composition using TPP-K (No. 6).

Japanese Patent Application No. 6-62030 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A quaternary phosphorus compound of the following general formula (1):

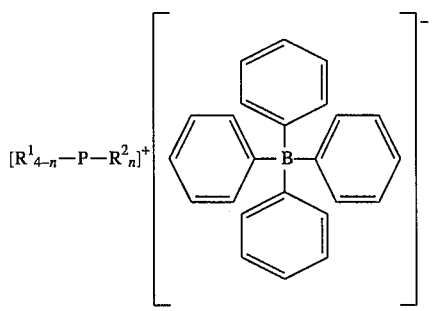

(1)

wherein $R^1$ is a group of the following formula (2):

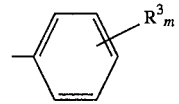

(2)

$R^2$ is a group of the following formula (3) or (4):

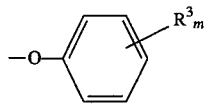

(3)

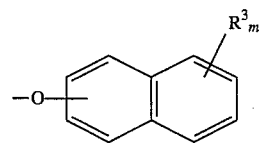

(4)

n is an integer of 1 to 4, $R^3$ is a monovalent hydrocarbon group having 1 to 6 carbon atoms, and m is an integer of 0 to 3, with the proviso that in formula (4) when m is at least 1, $R^3$ may be attached to either one or both of the aromatic ring having —O— and the aromatic ring free of —O—.

* * * * *